United States Patent
Kamprad

(10) Patent No.: US 8,642,639 B2
(45) Date of Patent: Feb. 4, 2014

(54) FORMULATION FOR L-TRYPTOPHANE COMPRISING CARBIDOPA/BENSERAZIDE

(75) Inventor: Joachim Kamprad, Rheine (DE)

(73) Assignee: Kamprad KG, Munster (DE)

( * ) Notice: Subject to any disclaimer, the term of this patent is extended or adjusted under 35 U.S.C. 154(b) by 1722 days.

(21) Appl. No.: 11/573,633

(22) PCT Filed: Aug. 12, 2005

(86) PCT No.: PCT/DE2005/001428
§ 371 (c)(1),
(2), (4) Date: Jun. 11, 2007

(87) PCT Pub. No.: WO2006/015590
PCT Pub. Date: Feb. 16, 2006

(65) Prior Publication Data
US 2011/0288145 A1    Nov. 24, 2011

(30) Foreign Application Priority Data
Aug. 12, 2004  (DE) .................. 10 2004 039 196

(51) Int. Cl.
*A01N 43/38* (2006.01)
*A61K 31/40* (2006.01)
*C07D 209/20* (2006.01)

(52) U.S. Cl.
USPC ......................................... 514/419; 548/496

(58) Field of Classification Search
USPC .......................................... 514/419; 548/496
See application file for complete search history.

(56) References Cited

U.S. PATENT DOCUMENTS

| 4,424,235 A | 1/1984 | Sheth et al. | 514/567 |
|---|---|---|---|
| 4,687,763 A * | 8/1987 | Wurtman | 514/53 |
| 5,188,840 A | 2/1993 | Iida et al. | 424/468 |
| 5,216,019 A | 6/1993 | Kamprad et al. | 514/419 |
| 6,207,699 B1 * | 3/2001 | Rothman | 514/419 |

FOREIGN PATENT DOCUMENTS

| DE | 3232873 | 3/1983 |
|---|---|---|
| EP | 0344158 | 12/1989 |
| FR | 2647345 | 11/1990 |
| FR | 2654931 | 5/1991 |
| WO | WO 88/04170 | 6/1988 |
| WO | WO 00/21504 | 4/2000 |

OTHER PUBLICATIONS

Kibbe, Handbook of Pharmaceutical Excipients, American Pharmaceutical Association, Pharmaceutical Press, London, United Kingdom, pp. 244-245, 2000.
Genazzani et al., "Effects of L-5HTP with and without carbidopa on plasma β-endorphin and pain perception: possible implications in migraine prophylaxis," *Cephalalgia: An International Journal of Headache*, 6:241-245, 1986.
International Search Report mailed Mar. 6, 2006.

* cited by examiner

*Primary Examiner* — Sreeni Padmanabhan
*Assistant Examiner* — Uma Ramachandran
(74) *Attorney, Agent, or Firm* — Cesari and McKenna, LLP

(57) ABSTRACT

The present invention relates to the use of L-tryptophan and a peripheral degradation inhibitor of L-tryptophan for the manufacture of a medicament for prevention or therapy of pain, depressions, sleeping disorders and other serotonin dependent diseases of the CNS, wherein L-tryptophan is present in a retarded and the peripheral degradation inhibitor is present in a non-retarded formulation.

5 Claims, 1 Drawing Sheet

FORMULATION FOR L-TRYPTOPHANE COMPRISING CARBIDOPA/BENSERAZIDE

This application is a national phase application under 35 U.S.C. §371 of International Application No. PCT/DE 2005/001428 filed 12 Aug. 2005, which claims priority to European Patent Application No.: DE 10 2004 039 196.3 filed 12 Aug. 2004. The entire text of each of the above-referenced disclosures is specifically incorporated herein by reference without disclaimer.

The present invention relates to the use of L-tryptophan and of a peripheral degradation inhibitor of L-tryptophan for the manufacture of a medicament for prevention or therapy of pain, depressions, sleeping disorders and other serotonin dependent diseases or disorders of the CNS, wherein L-tryptophan is present in a retarded and the degradation and the peripheral degradation inhibitor in a non-retarded formulation.

Processing of information and transmission occurs in the central nervous system (CNS) on the basis of neurochemical transmission. The chemical messenger molecules necessary therefore (neurotransmitter) are synthesised from nutrition components, usually amino acids, and are then available to the respective neural structures. Many diseases of the central nervous system are based upon a deficiency in one or several neurotransmitters in the CNS or are the consequence of lacking or defective bio availability of neurotransmitters. Examples of such messenger molecules are serotonin and dopamine.

Serotonin is prevalent in nature and is found in mammals in relatively high concentrations in the central nervous system (hypothalamus, periaquiductal grey, central grey substance, Limbic System), in the spleen, the lung and in the argentafine cells of the intestinal tract. The concentration in full blood is 0.1-0.3 µg/ml.

Serotonin has a peripheral effect on the smooth musculature of the vessels of the respiratory and gastrointestinal tracts. Serotonin exerts a particular significant effect on the central nervous system. Here it is involved among others in control of pain, control of spirit and regulation of sleep.

Dopamine is a catecholamine, which occurs among others in brain, adrenal gland and sympathetic nerve endings and which is a neurotransmitter of the hypophysiotrophic hypothalamus areas. The concentration of dopamine is reduced in the nuclei of the extra pyramidal motoric system in Parkinsonism.

Since neurotransmitters such as serotonin and dopamine can not be delivered directly to the CNS due to lacking passage through the blood brain barrier or due to significant side effects, biochemical precursors (precursors) are generally used.

The precursor L-dopa is generally administered in therapy of Parkinsonism in order to compensate for a systemic deficiency in dopamine in the CNS, in particular in the so called basal ganglia. However, L-dopa is already degraded into the principally desired neurotransmitter in the periphery to a high extent, i.e. in the blood as well as in the gastrointestinal tract but also at the blood brain barrier (BBB) and thus does not or only in insufficient amounts reach the CNS. As dopamine on its own can not pass the blood brain barrier, it floods the periphery but in fact does not enter the brain. This has the known peripheral side effects for consequence, such as nausea, vomiting, cardiac disorders, changes in blood pressure and so forth. In order to avoid these side effects and in order to increase the amount of L-dopa available to the CNS L-dopa is combined with peripheral degradation inhibitors, since L-dopa alike L-tryptophan is degraded peripherally by the amino acid decarboxylase. As a consequence, L-dopa is enriched in the plasma and can overcome in sufficient amount the blood brain barrier. There, L-dopa is degraded to dopamine as desired. Above that, L-dopa is peripherally metabolised by O-methyltransferase. However, the peripheral degradation pathway of L-dopa is only in part corresponding to the peripheral degradation pathway of L-tryptophan.

The precursor of the neurotransmitter serotonin is L-tryptophan, which is present in most proteins in 1-2%. L-tryptophan is present in the natural nutrition of human beings and is an essential amino acid. Different degradation pathways of L-tryptophan are known. The degradation of L-tryptophan in the liver via tryptophan-2-3-dioxygenase and via kynureninase is with over 90% quantitatively the most important one. In addition there is the peripheral degradation of L-tryptophan via 5-hydroxytryptophan (5-HTP) after decarboxylisation to 5-hydroxytryptamine (5-HT=serotonin).

L-tryptophan is used for therapy of pain with changing success. In addition L-tryptophan alone is applied for the treatment of sleeping disorders and depressions in tryptophan containing finished medicine products. Thereby, the nutrient L-tryptophan is added in excess, in order to increase by this means the formation of the "anti pain substance" serotonin in the CNS. However, efforts to use tryptophan on its own as efficient pharmaceutical are not really suitable despite partially extremely high doses of L-tryptophan or dietetic efforts with elimination of competing neutral amino acids at the blood brain barrier (competitive displacement).

Due to the peripheral degradation of L-tryptophan outside of the CNS serotonin is enriched at the wrong site, thereby resulting in undesired side effects such as blood pressure crisis, chronic diarrhoea, bronchospasm, cardiac disorders, gastrointestinal disorders and others. Only a small amount of L-tryptophan escapes peripheral degradation and can enter the central nervous system unhamperdly and can be degraded there to the desired neurotransmitter. Efforts to administer L-tryptophan in amounts as high as possible in order to achieve an effective enrichment of this amino acid failed due to the occurrence of side effects and due to an increased intracerebral and extracerebral degradation of serotonin and tryptophan. For this reason this amino acid has so far no practical significance for the treatment of, for instance, pain.

It is known, that Parkinson patients can be treated with L-dopa preparations in combination with the peripheral amino acid decarboxylase inhibitor benserazide and carbidopa and entacapon as O-methyltransferase inhibitor, respectively (COMT-inhibitor). The combination of L-dopa and the specific decarboxylase inhibitor benserazide together with a hydrocolloid and some conventional adjuvant as preparation with delayed agent release is described in DE 32 32 873. However, the relatively quick degradation of the agents in blood has negative effects. However, in order to provide a permanent availability of L-tryptophan at the blood brain barrier the administration of the agents either in high concentrations or in relatively short time intervals is indicated. However, the high concentration of the peripheral degradation inhibitor exhibits significant side effects, whereas the administration in short time intervals or a permanent administration necessitates a stationary administration.

The combination of L-tryptophan with a peripheral degradation inhibitor such as benserazide and carbidopa in a delayed release form for treatment of pain is described in EP 0 344 158 B1. Since it is known that benserazide and carbidopa are relatively quickly degraded in blood plasma (short plasma half lifer), a retarded release of both L-tryptophan as well as of the peripheral degradation inhibitors is described for a particular pharmaceutical form. Thereby the permanent supply of L-tryptophan to the blood brain barrier (in retarded form) is supported by a permanent supply of a peripheral degradation inhibitor (benserazide or carbidopa, in retarded form as well).

However, administration of agents in retarded form necessitates a relative complex formulation, which is in not to few cases associated with toxic additives. In addition, it is necessary to formulate the tablet, capsule, or solution in order to allow for oral administration. Furthermore, along with the retarded peripheral degradation inhibitor severe side effects occur. Thus, the patients suffer among others from day fatigue, nausea and skin irritations.

Thus, the problem underlying the present invention is to provide a pharmaceutical preparation which is easy to administer and which is largely free of side effects, for the treatment of pain, depression, sleeping disorders or other serotonin dependent disorders of the CNS.

The present invention relates to the use of L-tryptophan and a peripheral degradation inhibitor of L-tryptophan for the manufacture of a medicament for prevention or treatment of pain, depressions, sleeping disorders or other serotonin dependent disorders of the CNS, wherein L-tryptophan is present in a retarded and the peripheral degradation inhibitor is present in a non-retarded formulation. The peripheral degradation inhibitor may be a peripheral amino acid decarboxylase inhibitor and/or a kynureninase inhibitor and/or a tryptophan-2-3-dioxigenase inhibitor. Preferably, the peripheral degradation inhibitor is a peripheral amino acid decarboxylase inhibitor, in particular (2S)-3-(3,4-dihydroxyphenyl)-2-hydrazinyl-2-methyl-propanoic acid (carbidopa) or DL-serine-2-(2,3,4-trihydroxybenzyl)hydrazide-hydrochloride (benserazide).

Administration of L-tryptophan increases the central serotonin metabolism and the serotonin levels in the central nervous system, respectively. An increased serotonin level can be used therapeutically or preventively in particular for pain, depressions, sleeping disorders and other serotonin dependent disorders of the CNS. L-tryptophan (indolyl-3-alanine) represents a physiological compound (essential amino acid) which is used for the treatment of, for instance, sleeping disorders, depressions, pain and psychotic side effects of the L-dopa therapy of Parkinsonism.

The combination of L-tryptophan in delayed release agent formulations (retarded formulations) along with a peripheral degradation inhibitor of tryptophan is of great importance for the treatment of said diseases due to the uptake mechanism of the blood brain barrier.

Preferably, L-tryptophan amino acid decarboxylase inhibitors and/or kynureninase inhibitors and/or tryptophan-2-3-dioxygenase inhibitors are used as peripheral degradation inhibitors for L-tryptophan in the present invention. In particular, (2S)-3-(3,4-dihydroxyphenyl)-2-hydrazinyl-2-methyl-propanoic acid (carbidopa) or DL-serine-2-(2,3,4-trihydroxybenzyl)hydrazide-hydrochloride (benserazide) are preferred.

Amino acid decarboxylase inhibitors act by inhibiting the enzyme aromatic amino acid decarboxylase. Furthermore, the used peripheral decarboxylase inhibitors benserazide and carbidopa are also inhibitors of the kynureninase and tryptophan-2-3-dioxygenase and yield via all 3 metabolism pathways (in contrast to L-dopa) increased L-tryptophan scores in plasma.

A permanently high concentration of carbidopa or benserazide in form of a retarded agent release with inhibition of all three metabolism pathways of L-tryptophan (decarboxylase, kynureninase and 2-3-dioxygenase) is against all initial assumptions not necessary due to the surprisingly found results of the inventor with regard to the optimal utilisation of the inhibition of peripheral L-tryptophan degradation.

The peripheral degradation inhibitor can be administered simultaneously with, prior or after L-tryptophan.

The present inventive use of retarded L-tryptophan in combination with non-retarded peripheral degradation inhibitor has the following advantages: the medicament according to the present invention with only one retarded component circumvents the difficulties with the final formulation with two retarded components. As a consequence, the development efforts are lower; the pharmaceutical form is less complex and simpler. Possible toxological problems; which can result from the carrier and additives of the retardation additives, are avoided. The tablet or capsule may be manufactured in significantly smaller form, thereby becoming easier to be orally administered. The agents may be administered to the patient in form of a capsule, tablet, solution, inhalant or another generally used pharmaceutical form. Due to the simpler galenism the pharmaceutical form is more cost effective. Fewer side effects occur and the pharmaceutical form is more acceptable.

The following figures illustrate the invention.

EXAMPLE 1

Figure 1:
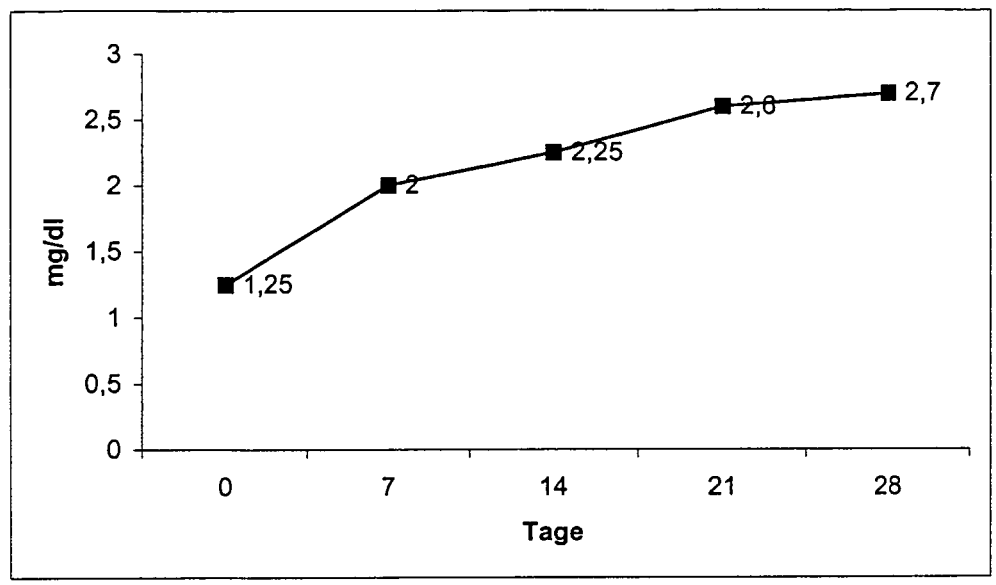
FIG. 1 shows a graphical representation of the results of the administration of L-tryptophan and benserazide, in each case reflecting retardation, from a study with 36 patients, wherein only those patients, which received the medicament and not the placebo, were included in the figure. The tryptophan plasma level is indicated in mg/dl.
Figure 2:
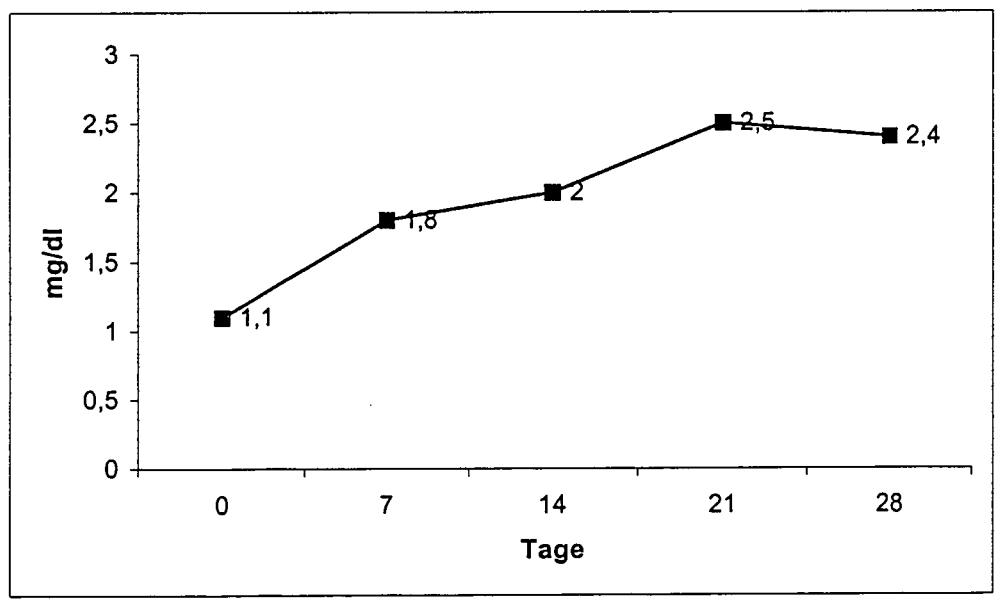
FIG. 2 shows a graphical representation of the results of the administration of L-tryptophan and benserazide, wherein only the administration of tryptophan reflects a retardation and benserazide was administered in non-retarded form out of a study with 5 patients. The tryptophan plasma level is indicated in mg/dl.

Administration of Retarded L-tryptophan and Retarded Benserazide 2 studies with all together 58 pain patients in 2 test centers were carried out with retarded L-tryptophan and retarded benserazide. The studies were double blind and randomized. One study was carried out in the Weserlandklinik in Vlotho, Germany, with 22 patients (12 verum, 10 placebo) with indication fibromyalgia. A second study with 36 patients (18 verum, 18 placebos) was conducted in the pain clinic of the Jakobi hospital in Rheine, Germany. In the second study patients with chronic pain were treated independently of the disease underlying the chronic pain. The agents L-tryptophan and benserazide were administered frequently and in small doses in order to achieve a steady state (also at night) of both active substances in the plasma. The kind of administration reflects the administration of agents in retarded form. Thus, the results can be equated with the administration of agents in retarded form. The subjects received evenly distributed over the day at 7, 10, 13, 16 and 19 o'clock 5 times two-piece capsules at 200 mg L-tryptophan/20 mg benserazide and at 22 o'clock two retard tablets at 200 mg L-tryptophan/25 mg benserazide. The tryptophan plasma levels were continuously monitored for four weeks. The L-tryptophan level in the plasma increased in both studies continuously, reaching its maximum with 2.6-3.4 mg/dl after 2-3 weeks and remaining constant thereafter.

EXAMPLE 2

Administration of Retarded L-tryptophan and Non-retarded Benserazide

In a further study the effect of the degradation inhibitor on the L-tryptophan plasma level was studied. Therefore, L-tryptophan concentrations identical to the concentrations of the first studies (see example 1) were administered to 5 subjects. Accordingly, the trial persons received evenly distributed over the day at 7, 10, 13, 16 and 19 o'clock 5 times two-pieces capsules at 200 mg L-tryptophan and at 22 o'clock 2 retard tablets at 200 mg L-tryptophan. In contrast, the peripheral degradation inhibitor was administered only at 3 time points reflecting a non-retarded administration. By this means benserazide was administered at 7, 15 and 22 o'clock in a dosage of 80 mg per single dose, that all together 240 mg benserazide were received per day (corresponding to the total amount of the two primary studies). Here, the plasma tryptophan level increased continuously as well and reached its maximum with average 2.5 mg/dl after 3 weeks and remained then until after 4 weeks constant. In contrast to example 1 almost no side effects occurred.

Result:

The studies show that aside of a prominent pain effect attributable to L-tryptophan the continuous delivery (corresponding to an administration in retarded form) of L-tryptophan is necessary for an optimal effect and a constantly high plasma level. In addition, the studies showed that for a constantly high tryptophan plasma level and consequently for an optimal effect of L-tryptophan the peripheral degradation inhibitor has not necessarily to be present in the plasma. It was not necessary to administer benserazide in retarded formulation as well. The established tryptophan plasma levels were after about 3 weeks constantly high and correlated with a prominent analgesic effect. Fewer side effects occurred, the acceptability was significantly better.

The invention claimed is:

1. A method for therapy of pain comprising administering to a subject in need thereof L-tryptophan and benserazide, wherein L-tryptophan is present in a retarded formulation and the benserazide is present in a non-retarded formulation.

2. The method according to claim 1, wherein the benserazide is administered simultaneously with L-tryptophan.

3. The method according to claim 1, wherein L-tryptophan and/or the benserazide is comprised in a capsule, tablet, or solution, or is formulated as an inhalant.

4. The method according to claim 1, wherein the benserazide is administered prior to L-tryptophan.

5. The method according to claim 1, wherein the benserazide is administered after L-tryptophan.

* * * * *